US008235959B2

(12) United States Patent
Ponomarenko et al.

(10) Patent No.: US 8,235,959 B2
(45) Date of Patent: Aug. 7, 2012

(54) ABSORBENT ARTICLE WITH COMPOSITE SHEET COMPRISING ELASTIC MATERIAL

(75) Inventors: Ekaterina Anatolyevna Ponomarenko, Bad Soden (DE); Mattias Schmidt, Idstein (DE); Tina Brown (née Lehmann)r, Cincinnati, OH (US); Alexander Eberhard Unger, Kelkheim (DE); Alexander Berk, Frankfurt am Main (DE); Darrell Ian Brown, Mason, OH (US); Blanca Arizti, Frankfurt am Main (DE)

(73) Assignee: The Procter Gamble Company, Cincinnati, OH (US)

( * ) Notice: Subject to any disclaimer, the term of this patent is extended or adjusted under 35 U.S.C. 154(b) by 527 days.

(21) Appl. No.: 12/329,002

(22) Filed: Dec. 5, 2008

(65) Prior Publication Data
US 2009/0157035 A1 Jun. 18, 2009

Related U.S. Application Data

(60) Provisional application No. 61/013,493, filed on Dec. 13, 2007.

(51) Int. Cl.
*A61F 13/15* (2006.01)
*B31F 1/12* (2006.01)
(52) U.S. Cl. ......... 604/385.24; 604/385.25; 604/385.26; 604/385.28; 604/385.29; 604/385.3; 156/183
(58) Field of Classification Search ............. 604/385.24, 604/385.25, 385.26, 385.27, 385.28, 385.29, 604/385.3; 156/163, 183
See application file for complete search history.

(56) References Cited

U.S. PATENT DOCUMENTS

| 4,573,986 | A | | 3/1986 | Minetola et al. |
| 5,576,090 | A | * | 11/1996 | Suzuki ..................... 428/152 |
| 5,607,760 | A | | 3/1997 | Roe |
| 5,609,587 | A | | 3/1997 | Roe |
| 5,635,191 | A | | 6/1997 | Roe et al. |
| 5,643,588 | A | | 7/1997 | Roe et al. |
| 6,258,196 | B1 | | 7/2001 | Suzuki et al. |
| 6,310,154 | B1 | | 10/2001 | Babcock et al. |
| 6,315,806 | B1 | | 11/2001 | Torobin et al. |
| 6,482,191 | B1 | | 11/2002 | Roe et al. |
| 6,695,992 | B2 | | 2/2004 | Reneker |

(Continued)

FOREIGN PATENT DOCUMENTS
EP 1201212 A 2/2002
(Continued)

OTHER PUBLICATIONS
International Search Report, dated Mar. 12, 2009, 4 pages.

*Primary Examiner* — Jacqueline F. Stephens
(74) *Attorney, Agent, or Firm* — Kuthleen Y. Carter; John G. Powell

(57) ABSTRACT

A process is claimed for making a composite sheet useful as topsheet with one or more openings to receive fecal material useful for an absorbent article, said composite sheet comprising a wrinkled, patterned elasticized region that comprises a patterned first sheet and an elastic material said first sheet being patterned with troughs, that are typically compacter, i.e. of higher density, prior to attachment to the elastic material. The troughs are attached to the elastic material. The resulting composite sheet has a uniform wrinkle pattern. Also claimed are specific absorbent articles. Also claimed are composite sheets with a specific residual strain and peel force value.

20 Claims, 6 Drawing Sheets

U.S. PATENT DOCUMENTS

| | | |
|---|---|---|
| 7,048,726 B2 | 5/2006 | Kusagawa |
| 2002/0049419 A1 | 4/2002 | Mizutani et al. |
| 2003/0181882 A1 | 9/2003 | Toyoshima et al. |

FOREIGN PATENT DOCUMENTS

| | | |
|---|---|---|
| EP | 1279388 A | 1/2003 |
| EP | 1 803 430 A | 7/2007 |
| WO | WO 95/24173 | 9/1995 |
| WO | WO 99/25283 A | 5/1999 |
| WO | WO 2005/103355 | 11/2005 |
| WO | WO 2005/112854 A | 12/2005 |
| WO | WO 2006/135357 A1 | 12/2006 |
| WO | WO 2007/074419 | 7/2007 |

\* cited by examiner

ABSORBENT ARTICLE WITH COMPOSITE SHEET COMPRISING ELASTIC MATERIAL

FIELD OF THE INVENTION

This invention is directed to a process to make a specific composite sheet, useful as or in a topsheet with one or more openings herein, said sheet having specific elasticized regions with improved wrinkle profile and absorbent articles comprising such specific (barrier) composite sheet materials.

BACKGROUND OF THE INVENTION

It is well known that fecal material is often difficult to remove from the skin of the user, in particular from sensitive skin such as by young babies and such as the skin around the genitals. Moreover, it is well known that fecal material on the skin can cause irritation and redness of the skin and sometimes even dermatitis of the skin.

One of the solutions to reduce the fecal material on the skin is to provide a means to isolate the fecal material immediately after discharge, away from the skin. For example, diapers with an elasticized topsheet with an opening also referred to as anal and/or genital cuff, through which the feces can pass to a void space between the topsheet and the absorbent core, have been developed. The fecal material is then stored underneath this topsheet, away from the skin. It may be particularly beneficial that such a topsheet is made of a material having barrier properties The inventors have found that often materials that provide a good barrier are not very comfortable in use. The inventors furthermore found that these barrier materials are sometimes difficult to elasticize, or that it is difficult to provide comfortable elastic regions in such materials. The inventors found that it may be desirable that the topsheet or other elasticized components (e.g., waistband, barrier cuffs, and leg cuffs) have softer elastic regions for the sensitive (baby) skin. It has been found that it is important that the wrinkles, caused by the elastic regions, leave less pressure marks. It has been found that the wrinkles should therefore be uniform. However, in some instances it may be difficult to produce elasticized articles with uniform elastics at high speed, especially when the elastics are applied in a curvilinear pattern and/or when the elastics are applied under high strain, and/or when the elasticized material is thick or stiff, such as may be the case with high barrier materials.

The inventors found that with prior art processes, the elastic material is merely attached in stretch state to a nonwoven with adhesives, which is applied in, for example, a spiral or omega pattern. Thus, the attachment of the elastic material in a stretched state may result in irregular attachment areas and irregular wrinkles.

The inventors have now found an improved process to provide comfortable elasticized regions in topsheet with one or more openings, and they have found an improved elasticized composite sheet material useful in or as such topsheets and useful in absorbent articles. In the improved process, a first sheet is submitted to a patterning step to form troughs, which are then simultaneously attached by application of gentle pressure to a stretched elastic material, i.e., before the elasticized region is allowed to relax and form wrinkles. The resulting patterned, wrinkled composite sheet material has an improved wrinkle pattern that is softer and/or more comfortable for the user. By patterning the first sheet with troughs and attaching these, or part thereof, to an elastic material prior to relaxation of the elastics, the subsequently wrinkle formation and wrinkle pattern can be controlled to have the desired uniformity.

SUMMARY OF THE INVENTION

The present invention relates to a process for making a composite sheet useful for an absorbent article, said composite sheet comprising a wrinkled, patterned elasticized region that comprises a patterned first sheet and an elastic material, said composite sheet being obtainable by:
  a) obtaining a first sheet;
  b) obtaining an elastic material that is at least partially stretched, having at least an average longitudinal direction of stretch;
  c) i) submitting said first sheet or part thereof to a patterning, pressure-applying step to obtain a patterned first sheet comprising troughs, and then positioning said at least partially stretched elastic material adjacent said patterned first sheet to obtain a combined material; or
     ii) positioning said at least partially stretched elastic material adjacent said first sheet to obtain a combined material and simultaneously or subsequently submitting the combined material, or part thereof, to a patterning, pressure-applying step to obtain a patterned combined material, comprising a patterned first sheet comprising troughs;
  d) simultaneously or subsequent to step c) attaching the formed troughs or part thereof, of the patterned first sheet to said elastic material, to obtain a stretched composite sheet comprising a patterned elasticized region;
  e) relaxing the composite sheet of step d) to obtain a composite sheet comprising a wrinkled, patterned elasticized region comprising wrinkles with peaks and valleys, said valleys being formed by both said elastic material and the troughs of said first sheet,
  whereby said composite sheet and optionally said first sheet comprises one or more openings, to receive fecal material, as described herein.

Whilst the process of the present invention may be used to make any composite sheet comprising an elastic material and a first sheet, or comprising even additional sheet materials, the process is particularly useful for making composite sheets that have (and the invention relates to composite sheets that have): a barrier first sheet, as described herein; a thick or stiff first sheet, having the bending rigidity as described herein; curved or angled elastics e.g., curvilinear elastics; elasticized regions, whereby adhesion of the elastic material and first sheet is achieved by application of pressure and optionally heat (and for example without adhesive present); and/or elastic material applied under high strain.

The process may for example be used to make composite sheets that comprise (and the invention relates to composite sheets that have) a first sheet that is a nonwoven sheet, comprising one or more nonwoven layers that is/are (each) a laminate of one or more spunbond and one or more meltblown webs; and/or a first sheet having the preferred hydrostatic head values and/or bending rigidity values, described herein.

In a preferred embodiment, the process comprises step c ii) and the first sheet and elastic material are positioned adjacent one another and simultaneously or subsequently the first sheet is patterned; preferably the attachment of the troughs is then simultaneously achieved.

In one embodiment, the surface of the first sheet that is not facing the elastic material is pressurized by, and optionally contacted by, a first patterning tool's surface having raised portions and the surface of the first sheet that faces the elastic material is pressurized and (indirectly) contacted by a second, non-mating surface of a tool, for example an even surface, e.g. said first tool's surface being the surface of a patterned roll with raised portions and the second tool's surface being the surface of an anvil roll.

The troughs of the first sheet (i.e., the portions of the first sheet that form the troughs) is more compact (i.e., has a higher density) than the portions of the first sheet not forming the troughs, e.g., the portions of the first sheet between neighboring troughs, including the crests and optionally portions of the first sheet that are not patterned and/or pressurized by the patterning tool.

It has furthermore been found that provision of a pattern with troughs in the first sheet and selectively attaching these troughs to the elastic material may allow effective attachment of the first sheet with a minimum of elastic material whilst this is in stretched state, and thus with a minimum surface area of the elastic material that is in the stretched state (and stays in stretched state, after relaxation of the composite sheet, loosing thus elasticity). Thus, optimum strength of the attachment of the elastic material to the first sheet can be achieved, whilst at the same time optimum elasticity can be maintained.

In one embodiment herein, the invention provides an absorbent article comprising a composite sheet that comprises a wrinkled and patterned elasticized region said region containing a first sheet and an elastic material said elasticized region having a residual strain of less than 30%, or less than 20% or between 2 and 20%, and in one embodiment, when a second sheet is present, as described herein, having a peel force of at least 1.4 N or at least 2.0 N, preferably at least 2.4N, or at least 3.0N and said elasticized region.

DETAILED DESCRIPTION OF THE INVENTION

Figure 1:
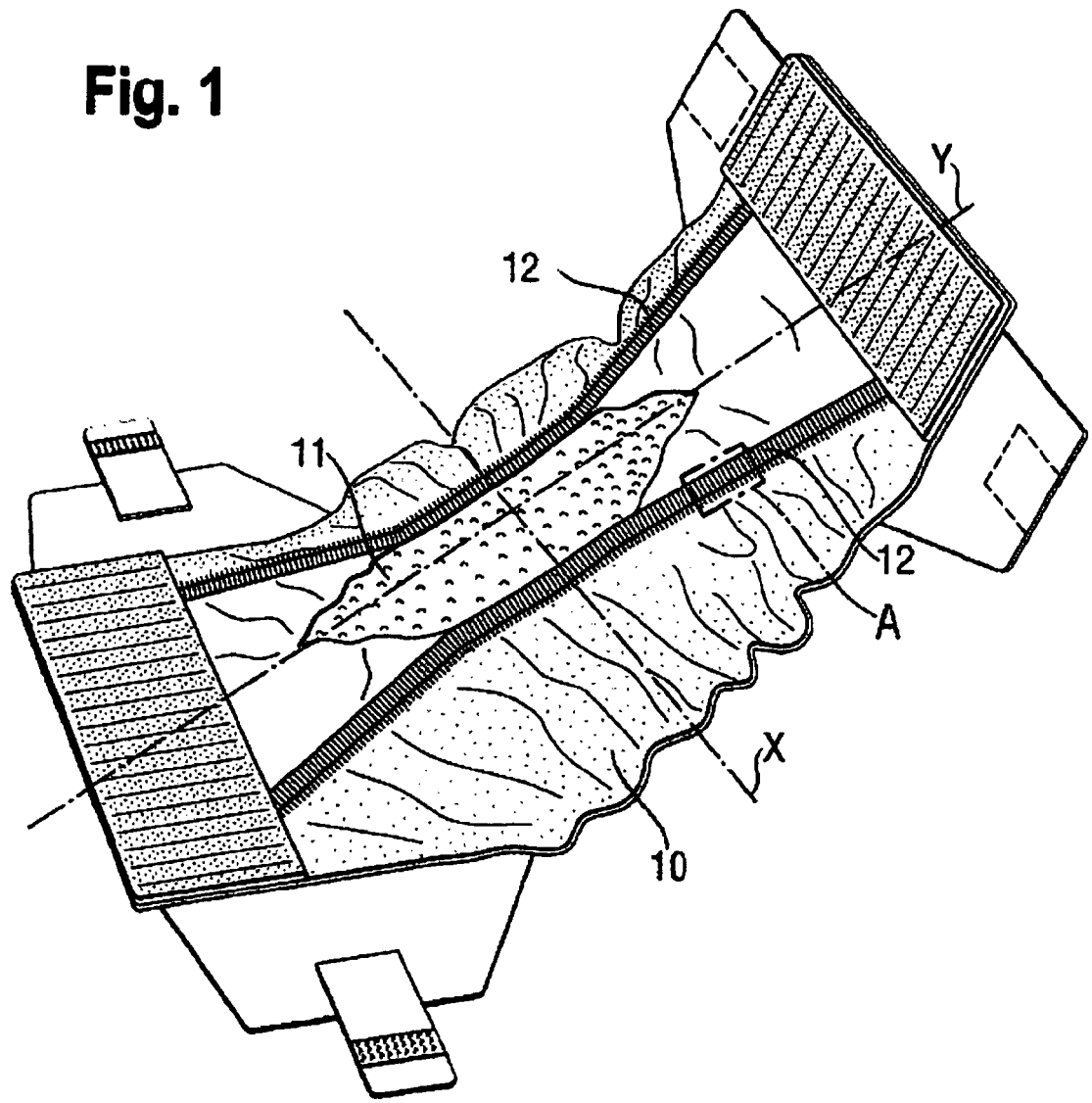
FIG. 1 shows a perspective view of a preferred absorbent article herein, comprising a composite sheet (10) having patterned, wrinkled elasticized regions (12).
Figure 1A:
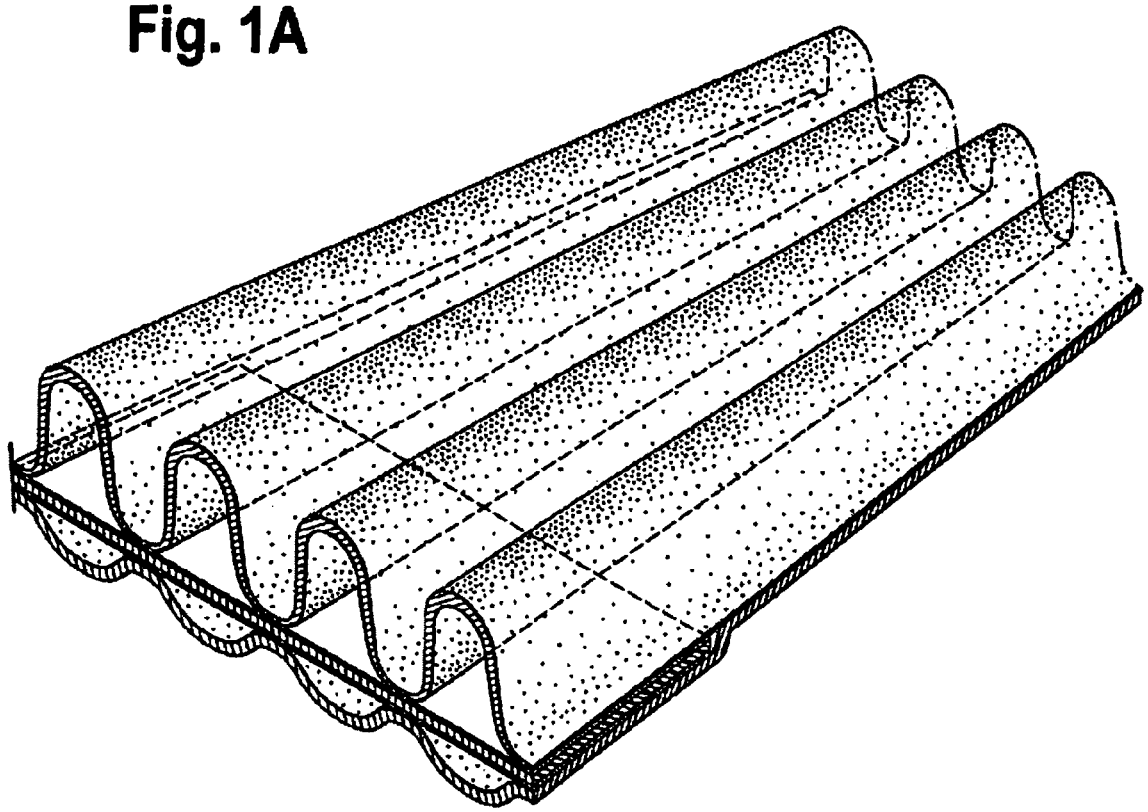
FIG. 1a shows a perspective view of portion A of the article of FIG. 1.

As used herein, the following terms have the following meanings:

"Absorbent article" means any article that can absorb body fluids and is suitable to be placed in close proximity to or against the skin of a user, e.g., the genitals and/or anus of the user, including without limitation, feminine hygiene articles; adult, baby or infant diapers or pads; including baby, infant, toddler diapers with fasteners, and so-called training or pull-up pants, and adult incontinence articles.

As used herein "front region" and "back region" refer to the two regions of an article, when the article is in use, respectively, closest to the front of the wearer and the back of the wearer.

As used herein, the term "void space" is a cavity in the article present in at least the relaxed state, which serves to accept and contain bodily exudates such as fecal material, for example, having a volume of at least 3 or even 5 $cm^3$ in relaxed state.

When used herein, "longitudinal" is the direction running substantially parallel to the maximum linear dimension of the sheet or article.

The "lateral" or "transverse" direction is perpendicular to the longitudinal direction and in the same plan of the majority of the article or composite sheet and the longitudinal axis.

"Substantially perpendicular" and "substantially parallel" include directions within 45° from the exact perpendicular or parallel direction, unless stated or specified otherwise.

"Direction of stretch" when used herein is considered the average direction of stretch.

As used herein, "along" means at least partially substantially parallel to and adjacent to.

"Adjacent" includes in "close proximity with" and "in contact with".

As used herein, "opening (11)" (as present in the composite sheet (10) or first sheet (13) or topsheet) means an area circumscribed by the sheet, but where the sheet material is not present, and which is large enough to receive fecal material, for example, being at least 2 cm long or wide, or having a surface area of at least 2 $cm^2$.

As used herein "relaxed" or "relaxed state" or "contracted" or "contracted state" means the state that no forces are applied to the article, to the composite sheet (10), to the elasticized region (12), or to elasticized topsheet or cuff herein (other than naturally occurring forces such as gravity), e.g., when the article is resting on a horizontal surface.

Composite Sheet (10) and Process for Making the Composite Sheet (10)

The composite sheet (10) herein is useful as a topsheet or a so-called anal cuff for absorbent articles, and it includes at least one opening to receive fecal material, as described herein in more detail.

The first sheet (13) may comprise one or more openings (11). The composite sheet (10) comprises at least a first sheet (13) and an elastic material (15). Where both the elastic material (15) and the first sheet (13) are present (e.g. one overlaying the other) an elasticized region (12) is formed. The first sheet (13) may be at least wider, in the transverse direction, then the elastic material (15). The first sheet (13) may also be attached to two or more elastic materials (15) to form two or more elasticized regions (12) in a composite sheet (10).

The composite sheet (10) and the first sheet (13) or part thereof (e.g., all or part of the area of the first sheet (13) forming the elasticized region) is patterned, comprising a multitude of troughs (16). This may be done by use of a patterning tool (30) that pressurizes, and optionally contacts, the first sheet (13) with raised portions extending from the surface (31) of the tool to form the troughs (16) of the first sheet. The first sheet (13), once present in the composite sheet (10), typically includes a multitude of troughs (16) and a multitude of crests (17).

The portions of the first sheet (13) forming the troughs (16) are typically compacted by this patterning step. The portion(s) of the first sheet (13) that include the compacted troughs (18) (or compacted attachment areas 18) may have a higher density than the portions of the first sheet (13) that does not include the compacted troughs (16), e.g., the crests (17) and/or non-patterned portions of the first sheet (13).

In one embodiment, the first sheet (13), or part thereof, is patterned during a patterning step and comprises troughs (16), but the elastic material (15) is not patterned and/or does not comprise troughs (16). In another embodiment, the elastic material (15) may be patterned less than the patterning of the first sheet (13), i.e., such that the troughs (16) of the elastic material (15) are shorter than the troughs (16) of the first sheet, e.g., at least 50% less. This may be applicable when the elastic material (15) comprises, e.g., a thermoplastic component and the patterning step involves the application of heat.

In a relaxed state, the patterned elasticized region (12) is a wrinkled elasticized region, due to the contraction forces of the elastic material (15) that cause the patterned first sheet (13) and patterned elasticized region (12) to wrinkle. Due to the patterning step, the valleys (22) of the wrinkles will coincide with the troughs (16) of the first sheet (13), as also further described herein (and the crests (17) of the first sheet (13) with the peaks (21) of the wrinkles).

The elastic material (15) is applied to the first sheet (13) in stretched or partially stretched state, the elastic material (15) is at least stretched to 150% or at least 200% of its fully contracted length, when applied to the first sheet; it may be stretched to at least 250% of its original, contracted length, or at least 300% or at least 330%, but for example less than 600%.

The elastic material (15) is positioned at least partially (e.g., at least 30% or at least 50% of its length), substantially parallel to the longitudinal direction Y. The elastic material (15) has an average direction of stretch or elasticity substantially parallel to the longitudinal direction. In one embodiment, the elastic material (15) is applied along a curvilinear pattern, for example, such that the elastic material (15) crosses each transverse axis (i.e., X-direction) of the composite sheet (10) only once. This is for example shown in FIG. 1.

The portion of the first sheet (13) that is submitted to the patterning step, or the first sheet (13) as a whole, is typically not elastic prior to the patterning step and the step applying the elastic material (15).

The patterned first sheet (13) comprises the pattern of troughs (16) over part or all of its length and/or over all or part of its width that forms the elasticized region (12). The first sheet (13) may also comprise the pattern outside the elasticized region (12).

Thus, the composite sheet (10) may have an elasticized region (12) with a pattern of troughs (16) along part or all of the transverse direction (X-direction) and along part or all of the length of the elasticized region (12). The elasticized region (12) may comprise at least one, or only one, trough (16) in the transverse direction X and for example at least 15 troughs (16), or at least 50 or at least 100, in the longitudinal direction (which is the direction of stretch of the elastic material and elasticized region). In certain embodiments, at least 10%, 30%, 40%, 60%, 75%, 90%, or even 100% of the length of the first sheet (13) that forms the elasticized region (12) comprises the pattern of troughs (16). For example, at least 30% of the width of the part of the first sheet (13) that forms the elasticized region (12) comprises the pattern of troughs (16), or at least 50% or even at least 70% or at least 80% or at least 90% or even about 100%. Furthermore, the width of the part of the first sheet (13) that comprises the troughs (16) may be more than the width of the elasticized region (12) (and more than the width of the elastic material (15)), for example be from 100% to 500% of the average width of the elasticized region (12), or from 100% to 250% or from 100% to 150%. The number of troughs (16) along the elasticized region (12) of the composite sheet (10) may vary; in one embodiment, the elasticized region (12), and thus the first sheet (13), has in the contracted state an average of from 5 to 25, 5 to 20, or 7 to 15 troughs (16) per cm.

Figure 4:
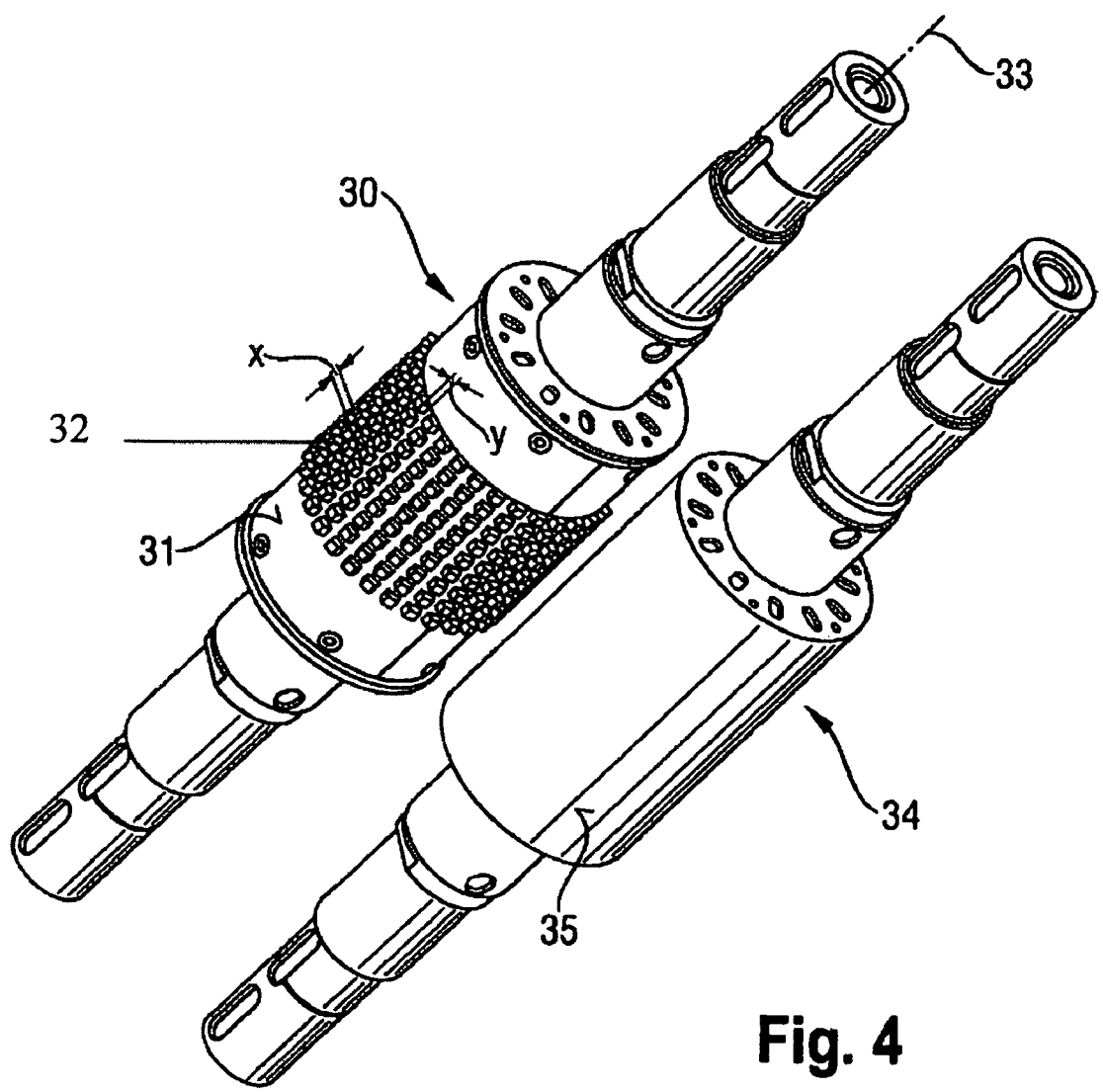
FIG. 4 shows a perspective view of a first tool and second tool that may be used herein to form the patterned composite sheet (10).
Figure 5:
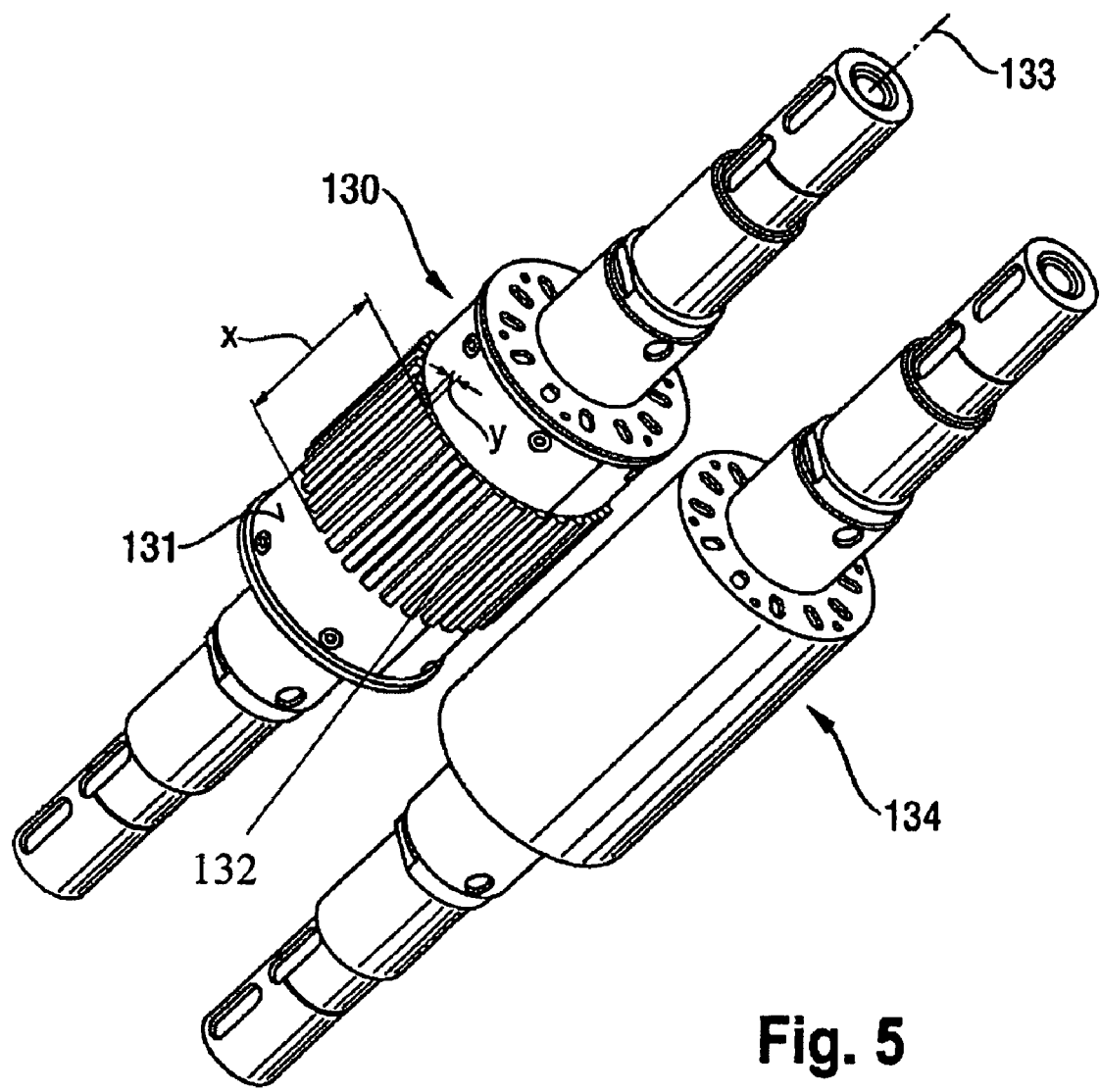
FIG. 5 shows a perspective view of an alternative first tool (30) and second tool that may be used herein to form the patterned composite sheet (10).

The patterning step may be done by applying (indirectly or directly) a patterning surface (31) of a first tool (30) to the surface of the first sheet (13) that does not face the elastic material (15) (but that faces typically in use the user's skin). The surface (31) of the first tool (30) may be a continuous surface, and the tool (30) is for example a patterned roll. The surface (31) of the first tool (30) comprises raised portions (with a first dimension x, parallel to the axis (33) of the first tool (30), as shown, for example, in FIG. 4). The raised portions may have any shape. For example, the raised portions may be configured as teeth (32), as shown in FIG. 4. In another example, the raised portions may be configured as ridges (132), as shown in FIG. 5.

The opposite surface of the first sheet (13), which faces the elastic material (15), is pressurized and for example indirectly contacted by a surface (35) of a second tool (34), to apply a counter pressure to the surface (31) of the first tool (30); the surface (35) of the second tool (34) is non-mating with the surface (31) of the first tool (30). The surface (35) of the second tool (34) may be a continuous surface such as an even surface of a substantially smooth roll. The surface (35) of the second tool (34) may comprise raised portions that contact the raised portions of the first tool (30), and which are non-mating with the raised portions of the first tool (30). The second tool (34) may be an anvil roll. The elastic material (15), or the second sheet (14) described herein after, may be directly contacted by the second tool (34).

The patterning step applies typically a pressure that is large enough to ensure patterning of the first sheet (13) and contacting of the troughs (16) with the elastic material (15) and, in one embodiment herein, aiding attachment thereof to the elastic material (15). The applied pressure may be limited, to avoid attachment of the crests (17) of the first sheet (13) to the elastic material (15). Suitable pressures may depend on the properties of the first sheet (13), including chemistry of the first sheet (13), bending rigidity, thickness, and on the type of elastic material (15), chemistry, thickness, and on whether for example adhesives are used. The pressure applied by the raised portions to the first sheet (13) and/or the second tool (34) may, for example, be from 10,000 to 100,000 psi, from 20,000 to 80,000 psi, or from 30,000 to 60,000 psi (obtainable by calculation). The average distance between the highest point of the raised portions (in the x-y plane) of the first tool (30) and the surface of the second tool (34) (or highest point on the surface (35) of the second tool (34)) may be from 0.01 to 1.0 mm, 0.025 to 0.6 mm, 0.025 to 0.5 mm, 0.025 to 0.3 mm, or 0.025 to 0.25 mm. As mentioned above, the patterning surface (31) of the first tool (30) comprises raised portions that may have any shape. The first tool (30) may be configured such that the total surface area in the x-y plane of the raised portions (i.e. the area that would contact a first sheet (13) without forming troughs (16) is smaller than the surface area in the x-y plane between the raised portions (e.g., less than 50% of the total surface area, less than 40%, or less than 30%). It may be that at least 5%, 10%, or 15% of the surface area of the surface (31) of the first tool (30) in the x-y plane is formed by the surface of the raised portions in the x-y plane. Alternatively, or in addition, the raised portions may be such that the distance between the highest points of neighboring raised portions in the y direction (e.g. in a direction substantially perpendicular to the transverse axis (33), as defined herein) is more than the average length dimension of the raised portions in the y direction, e.g. at least 20%, 40%, or 50% more. Average first, length dimensions of the raised portions may for example be from 0.01 mm to 3 mm, 0.05 to 2.5 mm, 0.05 to 2.0 mm, 0.1 to 2 mm, 0.1 to 1.5 mm, 0.1 to 1 mm, or 0.1 to 0.5 mm. Average width dimensions (x-direction) of the teeth (32) may, for example, be from 0.01 mm to 5 mm, 0.05 to 3 mm, 0.05 to 2.5 mm, 0.1 to 2 mm, 0.1 to 1.5 mm, 0.1 to 1 mm, or 0.1 to 0.5 mm. The width of the ridges (132) herein may be equal to the width of a trough (16) of the patterned elasticized region (12). In one embodiment, the first tool (30 or 130) comprises a surface (31 or 131) with raised portions in the form of ridges (132) or rows of teeth (32) that are placed substantially parallel to the axis (33, 133) of the first and second tools (30, 130, 34, 134), e.g. within 45°, or within 30° or within 20° or within 10° of the line parallel to the axis (33, 133).

In one embodiment herein, the average caliper of the first sheet (13) is less than 50% or less than 40% or less than 25% of the average distance between the raised portions of the first tool (30) in the y-direction. The surface (31) of the patterning tool (30) is directly or indirectly placed onto the first sheet (13). This may be such that the width of the tool (i.e., in the direction parallel to the axis (33), is within 45°, or within 30° or within 20° or within 10° of the average transverse direction (width) of the elasticized region (12) and/or elastic material (15). In one embodiment of the invention, the patterning step serves to adhere the elastic material (15) to the first sheet (13), optionally by use of heat bonding or ultrasonic bonding and/or by use of adhesive. The present process allows attachment and wrinkle formation that is independent of the bonding method used, e.g., independent of the adhesive pattern used. It is believed that the attachment of the first sheet (13) and elastic material (15) is in the process of the invention controlled by the patterning step and pattern thereof, and not by the adhesive pattern (as is typically the case in prior art processes for applying elastic material (15) to nonwovens).

The amount of adhesive used may be reduced without reducing the strength of the bonding of the elastic material to the first sheet (13). For example, less than 20 g/m² (per surface area of the first sheet (13) or of the elastic material (15)), 10 g/m², or 8 g/m² of adhesive may be used. The adhesive may be applied as very thin filaments or fibers, e.g., filaments of a diameter of less than 200 microns, or between 50 and 150 microns, as can be visualized in the elasticized region (12) of the composite sheet (10) by use of microscopy. Adhesives that may be satisfactorily used herein include adhesives manufactured by H. B. Fuller Company of St. Paul, Minn. and marketed as HL-1620 and HL-1358-XZP and adhesives from National Starch. The adhesive may be applied by known techniques, including spraying, or preferably melt-blowing. The adhesive may be applied in a pattern, such as a spiral or double spiral or omega pattern, or it may in one embodiment be applied randomly. However, it may be applied in a homogeneous amount per surface area, e.g. per cm². In one embodiment, the adhesive is applied as randomly oriented adhesive fibers in a homogeneous amount, e.g. as mentioned above. In one embodiment, use of adhesive may even be omitted, and the patterning step is used to apply pressure and optionally also heat, to achieve the partial attachment of the troughs (16) of the first sheet (13) with the elastic material (15). The resulting composite sheet (10) may thus have elasticized regions (12) that are free of adhesive.

In one embodiment, the patterning step applies heat to the first sheet (13) and/or to the elastic material (15), and the elastic material (15) and first sheet (13) are attached to one another by the heat and the pressure, (and optionally by adhesive). In this embodiment, it may be that the elastic material (15) comprises a thermoplastic component that adheres to the first sheet (13) under the process temperature of this step. The elastic material (15) may have an elastic component that is thermoplastic and adheres to the first sheet (13) under the process heat of the patterning step, and/or it may comprise an elastic component and a thermoplastic component, for example a thermoplastic coating on a elastomeric material, that adheres to the first sheet (13) under process temperature of the patterning step. Process temperatures may be between 30° C. and 165° C., or between 40° C. and 150° C. or 50° C. and 150° C. Preferred thermoplastic components are described herein below.

The process herein may also be done under cooling of the first sheet (13) and/or composite sheet (10), for example, by cooling the surface (31) (35) of the first or second tool (30) (34). For example, the process may be done such that the first sheet (13) and/or the resulting composite sheet (10) is contacted by a surface that is between −20° C. and 15° C. or between −20° C. and 10° C. or between −10° C. and 5° C. An example of a suitable apparatus for use herein includes a combination of a first tool (30) with a patterning surface (31) with raised portions and an opposing second tool (34), whereby the first and/or second tool (30, 34) comprise a cooling system.

The composite sheet (10) herein comprises, in a relaxed state, wrinkles whereof the peaks (21) are formed by the first sheet (13) and the valleys (22) are formed by the first sheet's troughs (16) and elastic material (15).

The composite sheet (10) may have an elasticized region (12) with a first sheet (13) with wrinkles that are uniform, e.g., a uniform wrinkle pattern. The wrinkles may have a uniform wrinkle height and/or uniform wrinkle density, namely:

a) at a partial elongation of the composite sheet (10) of ϵ, which is ⅔ (i.e. 66.7%) of its fully stretched length, the first sheet (13) present in the elasticized region (12) may have wrinkles with an average wrinkle height $H_w$ (as measured by the "Primos" method set out below, using PRIMOS equipment) of from 150 microns to 600 microns, or from at least 200 microns or from at least 300 microns and/or up to 550 microns, or up to 500 microns. This height is the distance between the highest point of a peak of a wrinkle to the lowest point of the valley of the wrinkle of the first sheet (13). The average wrinkle height above may have a standard deviation (STD) of less than 100 microns, preferably less than 75 microns, or less than 50 microns and the RSD (being the STD/$H_w$) is less than 30% or less than 20% or less than 10%.

b) Additionally or alternatively, at the elongation ϵ of ⅔ (=66.7%) of the fully stretched length (as set out above, and measured with the Primos method) the first sheet (13) of the elasticized region (12) of the composite sheet (10) herein may have wrinkles such that the average distance between the highest points of neighboring peaks, or between the centre point of the highest regions of neighboring peaks of the wrinkles is from 500 to 1500 microns, or from 750 to 1400 microns, or from 800 to 1300 microns or from 900 to 1200 microns, whereby the standard deviation may be less than 250 microns, or less than 200 microns or less than 100 microns. The RSD (=STD/average) may hereby be less than 30%, or less than 20% or less than 10%.

c) Additionally or alternatively, the elongation δ of ⅔ (=66.7%) of the fully stretched length (as set out above, and measured with the Primos method) the first sheet (13) of the elasticized region (12) of the composite sheet (10) herein may have wrinkles such that the average distance between the lowest points of neighboring valleys or between centre point the lowest regions of neighboring valleys of the wrinkles is from 500 to 1500 microns, or from 750 to 1400 microns, or from 800 to 1300 microns or from 900 to 1200 microns, whereby the standard deviation may be less than 250 microns, or less than 200 microns or less than 100 microns. The RSD (=STD/average) may hereby be less than 30%, or less than 20% or less than 10%.

d) Alternatively or additionally, at least 80% or at least 90% or even 100% of the wrinkles of the first sheet (13) (as defined above and measured above) have a wrinkle height between 650 microns and 200 microns, or between 600 microns and 250 microns, or between 500 microns and 300 microns; for example, less than 10% or even less than 5% of the wrinkles has a height of 700 microns or more.

e) Alternatively or additionally, at the elongation $\epsilon$ of $\frac{2}{3}$ (=66.7%) of the fully stretched length, the first sheet (13) of the elasticized region (12) herein may have an average wrinkle density of from 5 to 25, 6 to 20, 6 to 15, 6 to 10, or from 6 to 9 wrinkles per cm, as measured with the Primos method set out herein, and having a RSD of less than 30% or less than 20% or less than 10%.

In one embodiment, the first sheet (13) is folded around the elastic material (15) as a C-fold, and it thus serves as a covering sheet material, or herein referred to as a "second sheet (14)" disposed on the side of the elastic material (15) opposite the first sheet (13). Alternatively, or in addition, the opposite surface of the elastic material (15), not facing the first sheet (13) may be contacted and attached to an additional covering sheet material, i.e., second sheet (14). In one embodiment herein, the first sheet (13) and elastic material (15) are positioned adjacent a second sheet (14) in any of the process steps disclosed herein. The elastic material (15) may then be present between the first and second sheets (13, 14). The second sheet (14) may be present during the patterning step.

This second sheet (14) may thus be formed from the first sheet (13), or the second sheet (14) may be an additional sheet, made of any material that is pliable and can form wrinkles under the elastic forces of the elastic material (15), e.g., a nonwoven. In one embodiment, the second sheet (14) may include any nonwoven suitable for use as the first sheet (13). The second sheet (14) is typically attached to the elastic material (15) in a stretched state, by any method, including those described herein for the first sheet. The second sheet (14) may be patterned with valleys (22) and attached to the elastic material (15) with the valleys (22), by the process described herein for the first sheet (13). This may be done in a separate process step prior to or after the patterning process step of the first sheet (13), as described herein, or it may be done at the same time as the pattering step to pattern the first sheet (13). This may be done by use of the first tool (30) too, as described herein, or it may be done with a second tool (34) having raised portions whereof the top surface contacts the top surface of the raised portions of the first tool (30). In one embodiment, the second sheet (14) is combined with the elastic material (15) and the first sheet material (13) in step one or more of the steps described herein to form a combined material that is then pressurized by the first tool (30), as described herein, to form a pattern of troughs and valleys (16 and 22) in the first and second sheet (13 and 14), the troughs and/or valleys (16, 22) having for example the wrinkle uniformity as described herein. Either the second or the first sheet (14 or 13) may be contacted by the first tool (30).

Figure 2A:
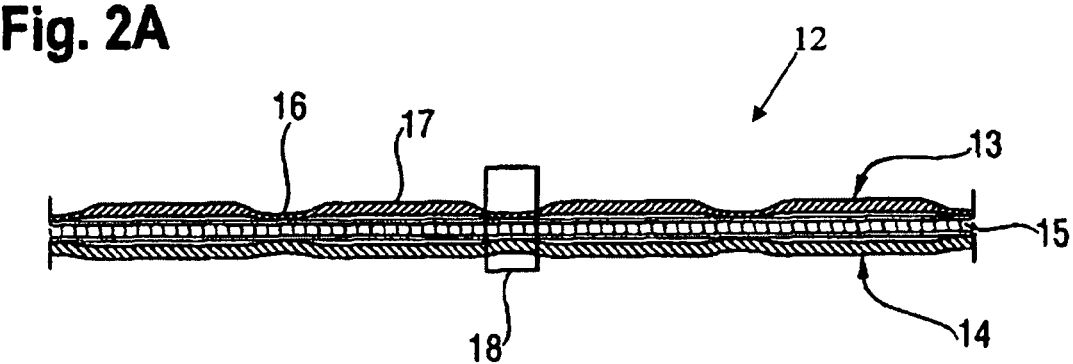
FIG. 2a shows a cross-sectional view of a fully stretched elasticized region (12) of a composite sheet (10) herein, having a first sheet (13) that is patterned.
Figure 2B:
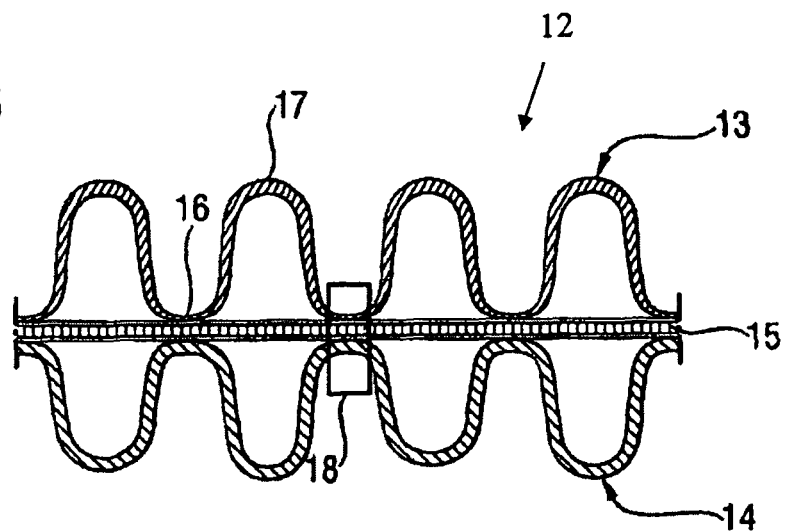
FIG. 2b shows the elasticized region (12) of FIG. 2a in partially stretched state.
Figure 2C:
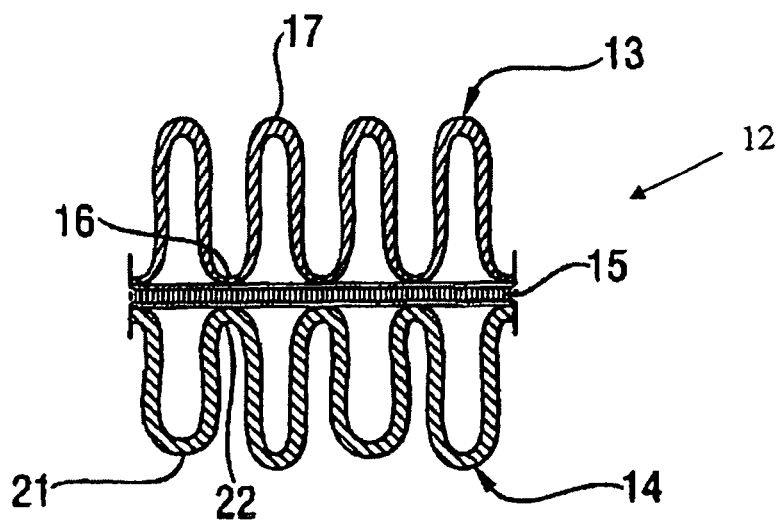
FIG. 2c shows the elasticized region (12) of FIG. 2a in contracted, relaxed state.
Figure 3A:
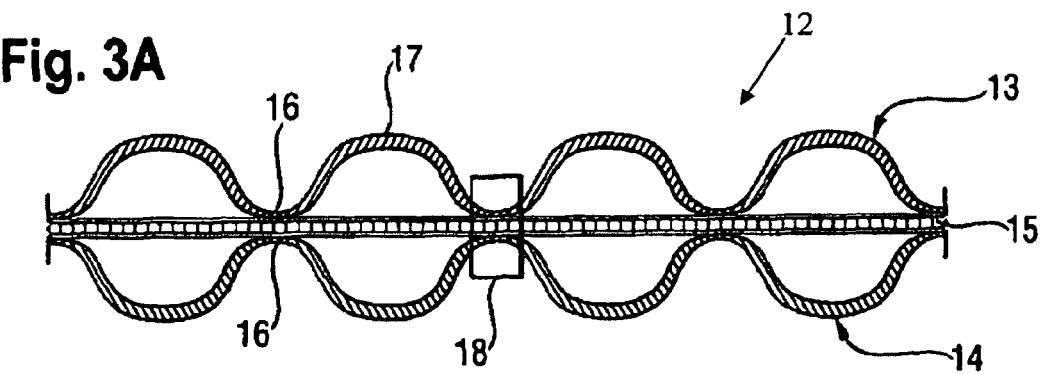
FIG. 3a shows a cross-sectional view of an alternative elasticized region (12) of a composite sheet (10) herein, in fully stretched state, having a first sheet (13) and a second sheet (14) that are patterned.
Figure 3B:
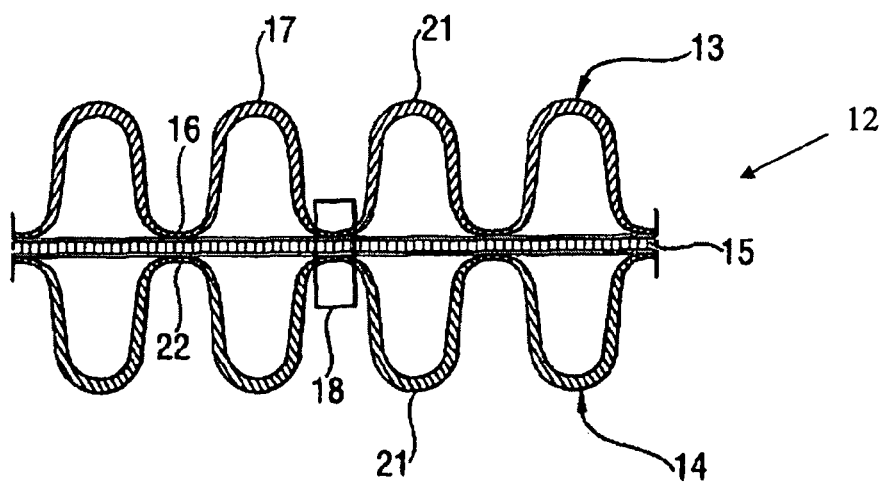
FIG. 3b shows the elasticized region (12) of FIG. 3a in partially stretched state.
Figure 3C:
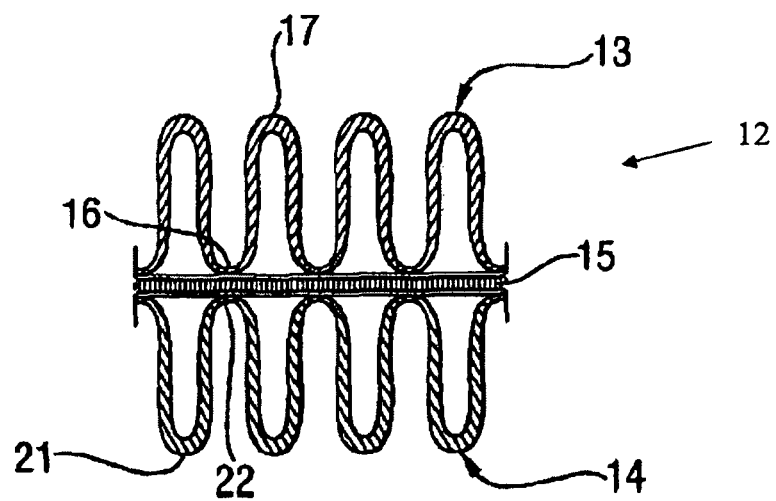
FIG. 3c shows the elasticized region (12) of FIG. 3a in contracted, relaxed state.

An embodiment whereby both sides of the elastic material (15) of the elasticized region (12) are contacted and adhered to, respectively a first sheet (13) and a second sheet (14) is shown in FIGS. 2a, b, c and 3a, b, c. As shown in FIG. 3a, b, c, the second sheet (14) may also be patterned as described herein, and this may or may not be the same pattern of valleys (22) as the pattern of troughs (16) of the first sheet (13). The second sheet (14) may also comprise valleys (22) that are compacted, having a higher density than the portions of the second sheet (14) that form the valleys (22) of the second sheet (14), just as described herein for the first sheet (13). The second sheet (14) may have the uniform wrinkle pattern as set out above. Alternatively, the second sheet (14) may have a non-uniform wrinkle pattern. The composite sheet (10) that comprises a wrinkled and patterned elasticized region (12) as described herein, having a first sheet (13) and any type of second sheet (14) may have a peel force of at least 1.4 N, preferably at least 2.0N or at least 2.4N, or at least 3.0N. The elasticized region (12) herein may have a residual strain of less than 30%, or less than 20%, or between 1% and 30% or between 5% and 20%, as measured by the method described herein below.

Elastic Material (15)

The elastic material (15) herein may be any elastic material (15) and it may be in any form or shape. The elastic material (15) may be in the form of a string, having a thickness to width ratio of 1:1 to 1:4, for example, having a substantially circular cross section, or it may be in the form of a band, having a thickness to width ratio of more than 1:4. The elasticized region (12) herein may comprise a multitude of strings or bands of elastic material (15). The elastic materials (15) used herein may be very thin, for example having a thickness or caliper (e.g. gauge) of up to about 200 microns, or even up to 150 microns or even up to 110 microns, or up to 100 microns. The elastic material (15) herein may have any minimum caliper, but it may be at least 20 microns, more preferably at least 40 microns, or even at least 60 microns, as defined herein. The elastic material (15) may have a thickness of about 70 to 100 microns. Suitable elastic materials (15) may be such that they provide the following elastic profile to the composite sheet (10):

1.5Lt by a first load force of less than 1.1N, 3.0Lt by a first load force of less than 2.1N and 4.5Lt by a first load force of less than 3.0N and a second unload force at 4.5Lt of more than 0.9N, a second unload force at 3.0Lt of more than 0.5N and a second unload force at 1.5Lt of more than 0.1N.

It may have an elastic profile of:

1.5Lt by a first load force of less than 1.1N, 3.0Lt by a first load force of less than 2.1N and 4.5Lt by a first load force of less than 3.0N and a second unload force at 4.5Lt of more than 0.9N, a second unload force at 3.0Lt of more than 0.5 and a second unload force at 1.5Lt of more than 0.1N. The elastic profile of the composite sheet (10) herein may be:

1.5Lt by a first load force of less than 0.6 N, 3.0Lt by a first load force of less than 1.1N and 4.5Lt by a first load force of less than 1.5N and a second unload force at 4.5Lt of more than 0.9N, a second unload force at 3.0Lt of more than 0.5N and a second unload force at 1.5Lt of more than 0.1N.

Hereby, Lt is the length of the composite sheet (10) or, (if the composite sheet (10) is a topsheet of the article, Lt is the shortened topsheet length), as can be determined as set out in EP1201212-A (referred to as shortened topsheet length). EP1201212-A also describes the test method to obtain the above and below elastic profile.

The elastic material (15) useful in the absorbent articles herein may be a so-called slow recovery elastomer, as described in co-pending application WO2005/020222 (EP application number 056760373.0). When used herein, the slow-recovery elastic is typically an elastomer which exhibits a normalized unload force at 37° C. of at least about 0.04 N/mm$^2$ as measured by the Two Cycle Hysteresis Test set out in the patent application. The slow recovery elastomer exhibits at least a 20% or at least 35% or at least 50% post elongation strain at 22° C. after 15 seconds of recovery, as measured by the Post Elongation Recovery Test set out in WO2005/020222. The slow recovery elastomer may comprise about 20% to about 70%, by weight, of at least one elastomeric polymer; and the remaining portion being components, such as those described below. The slow recovery elastomer may have a normalized unload force at 37° C. of at least about 0.16 N/mm$^2$ and at least a 10% post elongation strain at 22° C. after 15 seconds of recovery. The slow recovery elastomer may exhibit a normalized unload force at 37° C. of greater than about 0.04 N/mm$^2$ and a post elongation strain of at least about 20% after 15 seconds of recovery at 22° C., as described in the co-pending application. The slow recovery elastomer may exhibit a normalized unload force of greater than about 0.08 N/mm$^2$ at 37° C., or a normalized unload force of greater than about 0.12 N/mm$^2$ at 37° C. In other suitable embodiments, at 22° C., a suitable slow recovery elastomer exhibits a post elongation strain from about 75% to about 150% after 15 seconds of recovery; however, post elongation strain after 15 seconds of recovery may exceed about 170% at 22° C. Furthermore, the slow recovery elastomers may exhibit a specified post elongation strain at 22° C. after 30 seconds, 60 seconds, or three minutes of recovery. In certain embodiments, the slow recovery elastomer may exhibit at least about a 70% post elongation strain after 30 seconds of recovery at 22° C. In other embodiments, the slow recovery elastomer may exhibit at least about a 40% post elongation strain after 60 seconds of recovery at 22° C.

Suitable elastomeric polymers comprise styrenic block copolymers, natural and synthetic rubbers, polyisoprene, neoprene, polyurethanes, silicone rubbers, hydrocarbon elastomers, ionomers, and the like. Suitable elastic materials (15) include cross-linked elastic polymers, including cross-linked rubbers, for example, product code 2L-89, commercially available from Fulflex, (Limerick, Ireland). In one embodiment, the elastomeric polymer may be a block copolymer. A number of block copolymers may be used to prepare the slow recovery elastomer including multi-block, tapered block and star block copolymers. Generally, the block copolymers suitable for use in the slow recovery elastomer may exhibit both elastomeric and thermoplastic characteristics. In such block copolymers a hard block (or segment) may have a glass transition temperature ("Tg") greater than about 25° C. or is crystalline or semicrystalline with a melting temperature ("Tm") above about 25° C. The hard block may have a Tg greater than about 35° C. or is crystalline or semicrystalline with a Tm above about 35° C. The hard block portion is typically derived from vinyl monomers including vinyl arenes such as styrene and alpha-methyl-styrene or combinations thereof. Glass transition temperatures referred to herein are determined by tensile dynamic mechanical analysis performed in the linear elasticized region (12) of the material at a frequency of 1 Hz using a temperature ramp method. Suitably, film samples with a uniform thickness of about 0.3 mm or less may be used with a temperature ramp rate of about 1° C./min or slower. The tan δ peak temperature is taken as the Tg of the particular material or phase. Crystalline melting temperatures referred to herein are determined by Differential Scanning Calorimetry using a temperature ramp rate of 10° C./min. The melting endotherm peak temperature is taken as the Tm of the particular crystalline region. The block copolymers may comprise a soft block (or segment). The soft block generally exhibits a sufficiently low glass transition temperature and/or melting temperature so as not to form glassy or crystalline regions at the use temperature of the copolymer. In one embodiment, the use temperature may be between about room temperature (about 22° C.) and about body temperature (about 32° C.). However, other use temperatures are feasible and within the scope of this invention. Such soft blocks are generally physically incompatible with the hard blocks and form separate regions, domains, or phases. The soft block portion may be a polymer derived from conjugated aliphatic diene monomers. Typically, the soft block monomers contain fewer than about 6 carbon atoms. Suitable diene monomers include butadiene, isoprene, and the like. Particularly suitable soft block polymers include poly(butadiene) and poly(isoprene). Furthermore, it is envisioned that the soft block may be modified to tailor the Tg of the soft block. For example, a random copolymer of isoprene and styrene or a graft of styrene onto poly(isoprene) may be used. In such cases, lower amounts of the modifying resin may be used. Suitable block copolymers for use herein may comprise at least one hard block (A) and at least one soft block (B). In certain embodiments, the block copolymer may be an A-B-A triblock copolymer, an A-B-A-B tetrablock copolymer, or an A-B-A-B-A pentablock copolymer. Also, useful herein are triblock copolymers having endblocks A and A', wherein A and A' may be derived from different vinyl compounds. Suitable elastomeric polymers include styrene-olefin-styrene triblock copolymers such as styrene-butadiene-styrene (S-B-S), styrene-ethylene/butylene-styrene (S-EB-S), styrene-ethylene/propylene-styrene (S-EP-S), styrene-isoprene-styrene (S-I-S), hydrogenated polystyrene-isoprene/butadiene-styrene (S-EEP-S), and mixtures thereof. The block copolymers may be employed alone or in a blend of block copolymers. Particularly suitable block copolymers include styrene-butadiene-styrene (S-B-S) and styrene-isoprene-styrene (S-I-S) block copolymers. Such linear block copolymers of styrene-butadiene-styrene (S-B-S) and styrene-isoprene-styrene (S-I-S) are commercially available under the trade designation Vector from Dexco Polymers L.P., Houston, Tex., and under the trade designation Kraton from Kraton Polymers, Houston, Tex.

Modifying resins may be used; however, they should have a sufficiently high average molecular weight such that the Tg of the soft block is increased, resulting in an increase of post elongation strain at 22° C. after 15 seconds of recovery. The slow recovery elastomer may comprise the modifying resin in amounts from about 0% to about 60% by weight. The composition may comprise from about 20% to about 55% and even from about 35% to about 45% of the modifying resin. Suitable modifying resins useful herein may have glass transition temperatures ranging from about 60° C. to about 180° C., from about 70° C. to about 150° C., and from about 90° C. to about 130° C. Modifying resins useful herein include, unhydrogenated C5 hydrocarbon resins or C9 hydrocarbon resins, partially and fully hydrogenated C5 hydrocarbon resins or C9 hydrocarbon resins; cycloaliphatic resins; terpene resins; polystyrene and styrene oligomers; poly(t-butylstyrene) or oligomers thereof; rosin and rosin derivatives; coumarone indenes; polycyclopentadiene and oligomers thereof; polymethylstyrene or oligomers thereof; phenolic resins; indene polymers, oligomers and copolymers; acrylate and methacrylate oligomers, polymers, or copolymers; derivatives thereof; and combinations thereof. Preferably, the resin is selected from the group consisting of the oligomers, polymers and/or copolymers derived from: t-butylstyrene, cyclopentadiene, iso-bornyl methacrylate, methyl methacrylate, isobutyl methacrylate, indene, coumarone, vinylcyclohexane, methylstyrene, and 3,3,5-trimethylcyclohexyl methacrylate. Suitable modifying resins also include alicyclic terpenes, hydrocarbon resins, cycloaliphatic resins, poly-beta-pinene, terpene phenolic resins, and combinations thereof.

"C5 hydrocarbon resins" and "C9 hydrocarbon resins" are disclosed in U.S. Pat. No. 6,310,154. The slow recovery elastomer may exhibit temperature responsiveness. In one embodiment, a temperature responsive slow recovery elastomer may exhibit a post elongation strain after 15 seconds at 32° C. that is at least 35%, 50%, or even 75% less than the post elongation strain after 15 seconds at 22° C. It is believed that a slow recovery elastomer exhibiting temperature responsiveness may further facilitate diaper application. When the absorbent article is applied at about room temperature (e.g., approximately 22° C.), the slow recovery elastomer exhibits a relatively high degree of post elongation strain for a prescribed period of time. Upon application of the diaper, the slow recovery elastomer will rise in temperature because of the close proximity of the wearer's skin. As the temperature of the slow recovery elastomer increases and nears body temperature (e.g., approximately 32° C.), the reduced post elongation strain is exhibited. Temperature responsiveness allows for application of the diaper without "snap-back" while providing for increased recovery after application. Other components may be stabilizers, antioxidants, and bacteriostats (e.g., to avoid degradation of the slow recovery elastomer). Generally, the additive(s) may account for about 0.01% to about 60% or to about 25% or to about 10% of the total weight of the slow recovery elastomer composition. Other optional additives include thermoplastic polymers or thermoplastic polymer compositions which preferentially associate with the hard blocks or segments of the block copolymers. Without intending to be bound by theory, it is believed that these thermoplastic polymers become incorporated into the entangled three-dimensional network structure of the hard phase. This entangled network structure can provide improved tensile, elastic and stress relaxation properties of the elastomeric composition. Where the elastomeric polymer comprises a styrenic block copolymer, thermoplastic polymer additives such as polyphenylene oxide and vinylarene polymers derived from monomers including styrene, alpha-methyl styrene, para-methyl styrene, other alkyl styrene derivatives, vinyl toluene, and mixtures thereof, are useful in the present invention because they are generally considered to be chemically compatible with the styrenic hard blocks of the block copolymer.

Processing aids may also be included, such as processing oils, which are well known in the art and include synthetic and natural oils, naphthenic oils, paraffinic oils, olefin oligomers and low molecular weight polymers, vegetable oils, animal oils, and derivatives of such including hydrogenated versions, preferably a mineral oil. Viscosity modifiers may also be used, such as those well known in the art. For example, petroleum derived waxes can be used to reduce the viscosity of the slow recovery elastomer in thermal processing. Suitable waxes include low number-average molecular weight (e.g., 600-6000) polyethylene; petroleum waxes such as paraffin wax and microcrystalline wax; atactic polypropylene; synthetic waxes made by polymerizing carbon monoxide and hydrogen such as Fischer-Tropsch wax; and polyolefin waxes.

First Sheet (13)

The first sheet (13) may be any sheet material useful for absorbent articles, including woven sheets, nonwoven sheet, films. In a preferred embodiment, the first sheet (13) is not elastically extendable or stretchable, e.g. under normal process strain. In one embodiment herein, the first sheet (13) is a nonwoven sheet. The first sheet (13) may be a nonwoven sheet that is laminates of two or more nonwoven layers and/or two or more nonwoven webs. As used herein, a "nonwoven web" is a single web, whilst a "nonwoven layer" may comprise a multitude of nonwoven webs; a "nonwoven sheet" may comprise a multitude of nonwoven layers. The first sheet (13) may be a (nonwoven) barrier sheet, e.g., a first sheet(s) with a hydrostatic head value (measured with the hydrostatic head test set out herein) of at least 10 mbar, or at least 15 mbar, or at least 18 mbar, or in one embodiment, at least 20 mbar, or at least 25 mbar, or at least 28 mbar, or at least 30 mbar, or in one embodiment at least 35 mbar. In one embodiment, the hydrostatic head of the first sheet (13) is between 10 and 50 mbar. In one embodiment, the composite sheet (10) may alternatively or in addition have the hydrostatic head values above. The first sheet (13) or composite sheet (10) is considered to have the above hydrostatic head values if it has this value at any part of the first sheet (13) material, excluding elasticized areas (12) or areas with edges that are attached to other materials, prior to attachment to the elastic material (15) in the process herein; and/or if it has this value at any part of the first sheet (13) after attachment to the elastic material (15), i.e., the measurement is done on a sample of the sheet that does not comprise elastic material (15) or edges of the first sheet (13) that area attached to another material. In one embodiment, the first sheet (13) and/or composite sheet has a surface area free of elastics or edges of at least 2.5 cm×2.5 cm.

The first sheet (13) may have a bending rigidity of 20 grams or less, or 16 grams or less, or even 14 grams or less or 12 grams or less, as measured with the handle-o-meter test set out herein. Alternatively, or in addition the composite sheet (10) may have a bending rigidity of less than 35 grams, or less than 30 grams or less than 25 grams or less than 20 grams or less than 18 grams, or as described above. A first sheet (13) or composite sheet (10) herein is considered to have the above bending rigidity values if it has this value at any part of the material, excluding areas comprising elastic material, including the elasticized region (12) herein, or edges attached to other materials (these areas should not be included in the test). The bending rigidity as referred to herein, and measured with the method herein, is the rigidity of the sheet in any direction, unless specified otherwise.

In one embodiment, the first sheet (13) comprises at least one surface that is not to be attached to the elastic material (15) and that faces the patterning tool. The first sheet (13) may include a nonwoven web comprising fibers with an average fiber direction, and may have a bending rigidity of the values specified above, in the fiber direction. Preferred nonwoven webs that contact the patterning tool and/or that are on the surface of the first sheet (13) that is not attached to the elastic material (15), are spunbond webs (with fibers with an average fiber direction). The average fiber direction may typically be the longitudinal direction of the composite sheet (10) and/or the machine direction (MD) of the absorbent article.

The first sheet (13) or the composite sheet (10) has in one embodiment a low surface tension strike through value, as determined by the method described herein, of at least 30 seconds, or for example at least 50 seconds, or even at least 60 seconds. The strike through value may be less than 200 seconds, or less than 150 seconds or less than 100 seconds. A first sheet (13) or composite sheet (10) is considered to have the above low surface tension strike through values if it has this value at any part of the material, excluding areas comprising elastic material (15), including the elasticized region, or edges being attached to other materials.

As mentioned above, in one embodiment the first sheet (13) is a nonwoven sheet that comprises two or more nonwoven layers that are attached to one another, but in one embodiment, not fully (i.e. not 100%) laminated to one another. In one embodiment, the two (or more) nonwoven layers have an attachment area of 60% or less, or 40% or less or even 20% or less (of the total area of overlap between two neighboring nonwoven layers). In one embodiment, the first sheet (13) comprises two or more nonwoven layers that are attached to one another along the side edges of the overlap area, e.g. along the edges of each or one of the nonwoven webs (periphery) and optionally the area where elastic material (15) is present, and the nonwoven layer comprises areas, e.g. of at least 0.5 cm$^2$, where both layers are present but not attached to one another. In one embodiment, the first sheet (13) is such that at least two nonwoven layers thereof are only partially attached to one another and there is at least one area of 2.5×2.5 cm that is not attached (and does not comprise elastics or edges).

In one embodiment, the first sheet (13) is a nonwoven sheet that comprises nano-fibers, which have an average diameter of 1.0 microns or less. The first sheet (13) may comprise two or more nonwoven layers, whereof one or more, or each, comprise a nonwoven web that comprises such nano-fibers. The nonwoven sheet or layer or web may for example comprise at least 2 g/m$^2$ of nano-fibers, or at least 3 g/m$^2$ or at least 5 g/m$^2$ of nano-fibers. The nano-fibers may have an average diameter of 0.8 microns or less, or 0.6 microns or less. The nano-fibers may be made by known melt fibrillation methods or melt film fibrillation methods, such as described in U.S. Pat. No. 6,315,806 and U.S. Pat. No. 6,695,992. Suitable nano-fiber webs and layers are described in co-pending application WO2005/103355.

In one embodiment, the first sheet (13) is a nonwoven sheet that has at least one nonwoven layer, comprising at least one nonwoven web of meltblown fibers, for example present at a weight level of at least 5 g/m$^2$ by weight of the nonwoven layer, or for example at least 5.7 g/m$^2$, or at least 7 g/m$^2$, but for example less than 20 or less than 15 g/m$^2$ by weight of the nonwoven layer. The basis weight of the first sheet (13) is generally at least 5 g/m$^2$, or at least 7 g/m$^2$, or at least 10 g/m$^2$, or at least 17 g/m$^2$, or at least 22 g/m$^2$; the basis weight may be 60 g/m$^2$ or less, or 45 g/m$^2$ or less or 40 g/m$^2$ or less or 35 g/m$^2$ or less. If the first sheet (13) comprises two nonwoven layers, each comprising two or more nonwoven webs, the basis weight of each of the nonwoven layers present in the first sheet (13) may be 24 g/m$^2$ or less, or 22 g/m$^2$ or less or 18 g/m$^2$ or less, and/or at least 5 g/m$^2$ or at least 7 g/m$^2$ or at least 10 g/m$^2$.

Suitable first sheets herein are: a nonwoven sheet comprising a 17 or 22 gsm (g/m$^2$) SMMMS or SMMS nonwoven layer attached to (but not laminated to) another 17 or 22 gsm SMMMS or SMMS nonwoven layer (whereof for example the meltblown level of each layer is 5.7 or 7.3 gsm respectively), including for example a nonwoven sheet comprising 22 gsm SMMMS nonwoven layer, with for example 7.3 gsm meltblown fibers, attached to 17 gsm SMMMS or SMMS nonwoven layer, comprising for example 5.7 gsm meltblown fibers; a nonwoven sheet comprising a 17 gsm or 22 gsm SMS or SNS nonwoven layer, attached to another 17 gsm or 22 gsm SNS or SMS nonwoven layer, wherein "S" stands for spunbond, "M" for meltblown and "N" for nano-fiber.

The first sheet (13) may comprise a hydrophobic surface coating, such as known in the art, for example a wax, or preferably a hydrophobic surface coating comprising one or more silicone polymers or fluorinated polymers. Suitable silicone polymers are for example selected from the group consisting of silicone MQ resins, polydimethylsiloxanes, crosslinked silicones, silicone liquid elastomers, and combinations thereof. Typically, the molecular weight of such silicone polymers should be at least about 4000 MW, at least about 10,000 MW, 15,000 MW, 20,000 MW, or 25,000 MW. Suitable polydimethylsiloxanes are selected from the group consisting of vinyl-terminated polydimethylsiloxanes, methyl hydrogen dimethylsiloxanes, hydroxyl-terminated polydimethylsiloxanes, organo-modified polydimethylsiloxanes, and combinations thereof. Suitable fluorinated polymers are selected from the group consisting of telomers and polymers containing tetrafluoroethylene and/or perfluorinated alkyl chains. For instance, fluorinated surfactants, which are commercially available from Dupont under the trade name Zonyl®, are suitable for use herein. In particular, Zonyl® 321, 329, 8740, 9027, and 9360 are well suited for use in the present invention. Additionally, other Zonyl® materials include fluroadditives like micro-powders may be useful herein. These include, but are not limited to Zonyl® MP1100, MP1200, MP1400, MP1500J, MP1600N, TE-3667N (which is a water dispersion). The coating may be free of aminosilicones.

The compositions disclosed herein above may be deposited onto the composite sheet (10) in amounts of from at least about 0.01 gsm (gram of material/square meter of composite sheet), or from at least about 0.05 gsm, and or from at least about 0.1 gsm. First sheets (13) or composite sheets (10) are considered urine-impermeable and feces impermeable and thus suitable for use herein, when they have a low surface energy and a uniform pore size distribution, for example, with the low surface energy values, pore sizes, and air permeability values described in co-pending application EP-A-1417945. For example, useful may be materials that are substantially impermeable materials with an alcohol repellency of at least 5 or at least 6 or at least 7, or at least 8; having for example a surface energy of between 20 and 35 mN/m; optionally having a contact angle with water of above 100°; and optionally having a mean pore size of less than 50 microns, preferably less than 30 microns, or less than 20 microns, but optionally at least 2 microns, or at least 5 microns. The first sheet (13) or composite sheet (10) may have an air permeability of at least 3 Darcy, or at least 10 Darcy, or at least 20 Darcy, or at least 30 Darcy.

Absorbent Articles

An exemplary diaper with such a composite sheet (10)/topsheet is shown in FIG. 1. The absorbent article herein is an absorbent article to be worn in close proximity to (or in contact with) at least the anus of a wearer, such as adult incontinence products, such as briefs, pads or diapers, and baby diapers, toddler diapers, e.g. diapers with fasteners and pull-on diapers (or pants). The composite sheet (10) herein is or forms part of a topsheet of the article, that faces the wearer in use, e.g. such that the composite sheet (10) may contact the skin of the user. Thus, the topsheet comprises the composite sheet (10) or is formed by the composite sheet (10) or it may consist of the composite sheet (10). The composite sheet (10) or topsheet, and optionally the first sheet (13), has one or more (preferably one or two, most preferably one) openings (11) to receive fecal material. The opening is in the form of a single slit opening (11). The opening may be present in part of the front region of the topsheet (from the transverse axis X to the front of the diaper, and thus in use towards the front of the user) and in part of the back region of the topsheet. The topsheet may have a slit opening (11), which has a longitudinal dimension (length; Y-direction) substantially parallel to the longitudinal axis Y of the topsheet and of the article. The direction of stretch of the composite sheet (10) may be along the longitudinal axis. It may be that (in stretched state) the opening(s) (11) of the topsheet is (are) configured such that from 20% to 40%, or from 20% to 30% of the length of the opening (or total length of the openings) extends from the transverse axis of the topsheet towards the front edge of the topsheet, and the remaining percentage extends towards the back edge of the topsheet.

The dimensions and exact shape of the opening(s) (11) may vary, depending on the size of the topsheet and/or the absorbent article. For example, in certain embodiments the opening is in the form of a slit opening with substantially parallel longitudinal side edges, which are connected in the front and back by V-shaped or rounded V-shaped front and back edges, wherein both the front and back V-shaped edges comprise two angled edges. The maximum length of the slit opening (11) (in fully stretched state) may be for example 40% to 90% or 50% to 80%, or about 60% to 70%, of the total length L of the absorbent article. The average width of the opening (11) herein, in 66.7% stretched state, may be from 5% to 30%, or from 10% to 25%, of the average width of the topsheet (including opening width), or from a size 4 diaper, 15 mm to 60 mm, or from 20 mm to 40 mm.

The topsheet, being the composite sheet (10) or comprising the composite sheet (10), has the elasticized region (12) of the composite sheet (10) such that it extends along the longitudinal side edge of the opening(s) towards or completely to the front and/or back transverse edge of the topsheet. The elasticized regions (12) may be longer than the opening or openings (11). The topsheet comprising one or more openings (11), and being formed by the composite sheet (10) or comprising the composite sheet (10), may include at least two elasticized regions (12) as described herein, each along either longitudinally extending side edge of the opening or openings (11). The elasticized regions (12), and the side edges, may be mirror images of one another in the y-axis of the topsheet or article. The width of the elasticized regions (12) will vary, typically depending on the exact dimensions of the topsheet or cuff and/or the article. For example, the elasticized region (12) may have an average width of about 1 mm to 40 mm, or 2 mm to 30 mm, or 2 mm, or even 3 mm to 20 mm, or 5 to 12 mm (in relaxed, contracted state). The front end portions of two opposing elasticized regions (12) may bend away from one another (in the plane of the topsheet), so that the distance between the end edges of the opposing front end portions of two opposing elasticized regions (12) is larger that the distance between the two longitudinal centre points of two opposing elasticized regions (12), and equally, the distance between the end edges of the opposing back end portions of two opposing elasticized regions (12) may be larger that the distance between the longitudinal centre points of two opposing elasticized regions. This is further exemplified in FIG. 1. The front end portion of an elasticized region (12) may have an angle with a longitudinal line through the centre point of the elasticized region and parallel to the longitudinal axis of the topsheet, the angle being between 10° and 40°, or between 17° to 35°, or between 20° and 35°. The back end portion of an elasticized region (12) may also have an angle with a longitudinal line through the centre portion of the elasticized region (12) and parallel to the longitudinal axis of the topsheet, the angle being between 10° and 50°, or between 17° to 45°, or between 25° and 45°. When both front end portions and both back end portions have an angle as above, then the elasticized regions (12) have a so-called X-shape.

The composite sheet (10) or topsheet may have a crotch area, being the centre 30% of the topsheet, in longitudinal direction, and it may comprise one or more secondary elasticized regions in the crotch area, for example on either longitudinal side of the opening(s) (11) or part thereof, typically extending in longitudinal direction between a longitudinal side edge of the topsheet or composite sheet (10) and the elasticized region (12) (described above) closest to the edge. Such a secondary elasticized region may have an overall curvature, curving away from the closest elasticized region, described above. Just as the elasticized region (12) described herein above, the secondary elasticized region may be patterned and it may be obtainable by the process described herein, and the description of the elastic material (15), the process of patterning and the pattern obtained with respect to the elasticized region (12) is equally applicable to the secondary elasticized area Suitable elasticized regions (12) of the topsheet or composite sheet (10) may comprise a covering sheet, or second sheet (14), material on the side of the elastic material (15) of the region, that is not facing (and partially adhered to) the first sheet, as described above. The longitudinal side edges of the topsheet may be joined or attached to the longitudinal side edges of the backsheet, by any attachment means known in the art, to form longitudinal opposing attachment areas. In certain embodiments, the topsheet and the backsheet are attached directly to one another in some locations and are indirectly joined together in other locations.

The absorbent article of the invention may be sag-tolerable, and therefore include a topsheet that is sag-tolerable as defined and described in EP1279388-A.

Any portion of the topsheet may be coated with a skin care composition or lotion or powder, known in the art. A skin care composition or lotion may be present on the elasticized regions (12) herein, and optionally on the secondary elasticized regions. Examples of lotions include those described in U.S. Pat. No. 5,607,760; U.S. Pat. No. 5,609,587; U.S. Pat. No. 5,635,191; U.S. Pat. No. 5,643,588; WO 95/24173, provided the lotion is compatible with the elastic material (15), and does not destroy the elastic material (15) or reduce its elasticity.

Suitable absorbent articles herein may comprise a backsheet, an absorbent core, having a core coversheet facing the wearer in use, and one or more cuffs, such as barrier cuffs and/or leg cuffs, which may be elasticized and comprise patterned, wrinkled elasticized regions as described herein for the composite sheet (10) herein.

The backsheet may be liquid impervious, as known in the art. In certain embodiments, the liquid impervious backsheet comprises a thin plastic film such as a thermoplastic film having a thickness of about 0.01 mm to about 0.05 mm. Suitable backsheet materials comprise typically breathable material, which permit vapors to escape from the diaper while still preventing exudates from passing through the backsheet. Suitable backsheet films include those manufactured by Tredegar Industries Inc. of Terre Haute, Ind. and sold under the trade names X15306, X10962 and X10964. The backsheet, or any portion thereof, may be elastically extendable in one or more directions. The backsheet may be attached or joined to a topsheet, the absorbent core, or any other element of the diaper by any attachment means known in the art. It may desirable that the longitudinal side edges of the topsheet and backsheet are directly attached to one another, but that the longitudinal edges of the topsheet and the core are not attached to one another.

The absorbent core may comprise any absorbent material which is generally compressible, conformable, non-irritating to the wearer's skin, and capable of absorbing and retaining urine, such as comminuted wood pulp, creped cellulose wadding; melt blown polymers, including coform; chemically stiffened, modified or cross-linked cellulosic fibers; tissue, including tissue wraps and tissue laminates; absorbent foams; absorbent sponges; super absorbent polymers; absorbent gelling materials; or any other known absorbent material or combinations of materials; it may be desirable that the absorbent cores include more than 80% by weight of the absorbent core content (e.g. excluding core wrap) of absorbent gelling material or even be free of airfelt.

The absorbent article may also include a sub-layer disposed between the topsheet and the absorbent core, capable of accepting, and/or immobilizing bodily exudates, typically fecal material. Suitable materials for use as the sub-layer may include large cell open foams, macro-porous compression resistant non woven highlofts, large size particulate forms of open and closed cell foams (macro and/or microporous), highloft non-wovens, polyolefin, polystyrene, polyurethane foams or particles, structures comprising a multiplicity of vertically oriented, looped, strands of fibers, or apertured formed films, as described above with respect to the genital coversheet. (As used herein, the term "microporous" refers to materials that are capable of transporting fluids by capillary action, but having a mean pore size of more than 50 microns. The term "macroporous" refers to materials having pores too large to effect capillary transport of fluid, generally having pores greater than about 0.5 mm (mean) in diameter and more specifically, having pores greater than about 1.0 mm (mean) in diameter, but typically less than 10 mm or even less than 6 mm (mean).

The diapers herein may comprise a waistband, which may be an elasticized, waistband, comprising elasticized regions as described herein for the composite sheet (10) herein. The diapers herein may have a fastening system, typically joined to the waistband, as known in the art. Suitable fastening systems may include fastening tabs and landing zones, wherein the fastening tabs are attached or joined to the back region of the diaper and the landing zones are part of the front region of the diaper.

It may be desirable that the articles of the invention (e.g. diaper) when packed in their packaging material, comprise two transverse folds, so that when unfolded for use by the user or care taker, the article (e.g. diaper) is in a U-shape and easier to apply.

Test Methods

Handle-o-Meter Bending Rigidity Test

This method serves to determine the bending rigidity (and thereby softness) of a nonwoven layer or nonwoven sheet, as described herein, and reflects the flexibility and surface friction of the material. In this test, a nonwoven is deformed through a slot by use of a plunger, and the required force is measured. This method is based on the INDA Standard test IST 90.3-92

A sample material of the nonwoven sheet or nonwoven layer of 1 inch long and 1 inch wide (25 mm×25 mm) is cut and conditioned at 65% humidity and 21° C. as set out in the INDA test. The sample is free form elastic material (15) or edges attached to other materials. In one embodiment, the average fiber direction of the nonwoven web or layer in contact with the skin in use can be determined and this would be the Y direction (e.g. in use typically corresponding MD dimension of the absorbent article).

A handle-o-meter, available from Twingh-Albert Instruments Co., Philadelphia, USA, is calibrated as set out its user instructions.

The slot width is 6.35 mm.

The sample is placed under the plunger and on the slot with the surface that in use contacts or faces the skin up wards facing up. A first dimension is perpendicular to the slot and this is the direction tested, for which the bending rigidity is reported herein. In one embodiment, this is the average fiber direction of the skin-facing surface, e.g. the spunbond layer. The sample is centered over the slot and the test is run and the force is measured. This value is multiplied by 4 (e.g. normalised to a 4 inch×4 inch sample) and reported in grams herein as the bending rigidity.

Hydrostatic Head (Hydrohead)

The hydrostatic head (also referred to as hydrohead) as used herein is measured with a low surface tension liquid, i.e. a 49 mN/m liquid (solution).

This liquid is prepared as set out below.

This test is performed as set out in co-pending application WO2005/112854A, conform the Inda/Edana test WSP 80.6 (05). However, the water pressure (from below) is increased with a rate is 60 mbar/min.

A sample of 5 $cm^2$ is taken from the composite sheet, first sheet or topsheet herein. The sample should be free from elastic material (15) or edges that are connected to other materials.

The test head used has a 2.5 cm diameter; the protective sleeve used has a 2.2 cm diameter.

The test is performed on this sample and the Hydrostatic head value is obtained, and referred to herein.

49 mN/m (Dynes/cm) Liquid Preparation:

A 10 litre canister with tap is cleaned thoroughly 3 times with 2 litres polyethylene and then 3 times with 2 litres distilled/deionized water.

Then, it is filled with 10 litres distilled/deionized water and stirred with a clean stirring bar for 2 h, after which the water is released via the tap.

A 5 litre glass is cleaned 6 times with water and then 6 times with distilled/deionized water.

Then, 30.00 g of Na Cholate and 5 litres of distilled/deionized water are placed in the cleaned 5 litres glass. (Na Cholate should have a TLC purity of >99%, e.g. supplied by Calbiochem, catalog #229101). This is stirred with a clean stirring bar for about 5 min, until the Na Cholate is visibly dissolved.

The stirring bar is removed from the glass with a magnetic stick (without touching the solution) and then the Na Cholate solution is poured into the 10 litres canister and more distilled/deionized water is added such that the concentration of the final solution is 3 g/l. This is further stirred with a stirring bar for 2 hours and then used.

This preparation of the solution and use thereof is at the temperature stated for the test for which it is used, or if no temperature is stated, it is kept at 20° C.

The surface tension of the solution is measured and this should be 49 mN/m (±2). (The surface tension may be determined by method: ASTM D1331-56 ("Standard test method for surface and interfacial tension of solution of surface active agents") using a Kruss K12 tensiometer.)

Strike Through Value Method

The low surface tension strike through value referred to herein may be obtained by the Edana method WSP70.3 (05), except that a low surface tension liquid (see below) is used and a sample of 1 inch×1 inch (25 mm×25 mm) may be used. The sample should be free of elastic material (15) or of edges that are connected to other materials. The value obtained from this sample measurement is reported herein.

The low surface tension liquid is a liquid with a surface tension of 32 mN/m prepared as follows:

In a clean flask, 2.100 grams of Triton-X-100 is added to 500 ml distilled water (already in flask) and then 5000 ml distilled water is added. The solution is mixed for 30 minutes and then the surface tension is measured, which should be 32 mN/m.

(The surface tension may be determined by method: ASTM D1331-56 ("Standard test method for surface and interfacial tension of solution of surface active agents") using a Kruss K12 tensiometer.)

Method to Measure Wrinkle Profile/Uniformity (Primos Method)

The wrinkle dimensions, e.g. height, and the wrinkle densities, and uniformity thereof, as described herein, can be measured as follows.

The composite sheet (10) with the elasticized region (12) is removed from the absorbent article such that the elongation potential, wrinkle height and wrinkle density are not changed. (If the PRIMOS equipment and method below can be used directly on the absorbent article with the composite sheet (10), then the composite sheet (10) does not need to be removed.)

It is left for 24 hours at 25° C. and 50% humidity, prior to the elongation/stretching step below, which will be performed under the same conditions.

One or more samples are marked in the partially stretched composite sheet (10), or cut there from, if necessary in order to do the PRIMOS measurement, as follows: the composite sheet (10) is gently and evenly stretched, horizontally and on a flat surface, to its fully stretched length and then released until it has 66.7% (⅔) of said fully stretched length. Then, one or more samples are marked in the composite sheet (10). The 66.7% stretched sample may be any length, but for example a sample may have a dimension of 7.5 cm in the direction of stretch (e.g. 7.5 cm of the length of the composite sheet (10) in 66.7% stretched state). A sample should have the full width of the elasticized region (12), and if possible, the full width of the composite sheet (10).

Measurement of lengths of the sample can be done with for example a micrometer screw.

The partially stretched sample, having 66.7% of its fully stretched length (for example a sample of 7.5 cm) is then examined by use of PRIMOS equipment and its data acquisition software, following the manufacture's instructions manual, using a 13×18 mm lens.

The PRIMOS equipment and software will measure all peak heights, widths etc and the herein described values can be calculated there from. The height is the distance between the highest and lowest point of a peak. It should be noted that "shoulder peaks" are not regarded peaks of the wrinkles herein, as is a known approach in the art. Namely, if two adjacent peaks, A and B, are joined by a valley and either a) the distance from the highest point of peak A to the lowest point of the valley is less than 30% of the height of peak A or b) the distance from the highest point of peak B to the lowest point of the valley is less than 30% of the height of peak B, then said peak B is considered a shoulder peak and not an individual peak, and thus peak A and B are considered a single peak A (e.g. with a single width, single height etc.). Thus, if either a) or b) above applies, A and B are taken as one single peak.

Residual Strain

The residual strain of an absorbent article or of a composite sheet (10), obtainable by the process herein can be calculated as follows.

The elastic material (15) is conditioned as above. The contracted, relaxed length of the elastic material (15) or elasticized region (12) as used in the process to form the composite sheet (10) herein is determined. This is $l_0$.

Then, the length of the elastic material (15) or elasticized region (12) in the contracted absorbent article or composite sheet (10), conditioned as set out in the method above and on a flat surface, is measured. This is $l_x$.

Then, the residual strain $S_r=[(l_x-l_0)/l_x]$ can be calculated.

For example, if 10 cm elastic material (15) is attached to a first sheet (13) over a length of 40 cm, and the resulting composite sheet (10) has a contracted length of 15 cm, then the residual strain is (15−10)/15=33.3%.

In a finished article, the residual strain can be calculated if the elastic material (15) can be removed from the article and then, the contracted length thereof can be calculated as above. (This of course after having calculated $l_x$)

Peel Force Method

This method serves to determine the strength of the bond in the composite sheet (10) of the elastic material (15) and the first sheet (13 and second sheet (14); the herein reported peel force is the force required to undo the bond of (delaminate) the elastic and the sheets.

The measurement may be done with for example a Zwick 2.5 KN tensile tester with a load cell of 50N. The test path is 100 mm. The speed is set to be 100 mm/min. The clamps are for example 25 mm×40 mm. the target gage length can suitably be set, e.g. 25 mm. (N.B.: In general, the load cell should be chosen in a way that the expected measurement values are in the calibrated range of the capacity of the load cell (e.g. 0.2-100% of capacity, which is for a 50 N load cell from 0.1 N-50 N)).

A sample is cut from the composite sheet (10) such that the whole width of the elasticized region (12) (and of the elastic material (15)) is comprised in the sample and such that at one longitudinal side (in direction of stretch) an area is present that is formed by the first and second sheet material, but not by the elastic material.

A JDC precision Sample cutter by Thwings-Albert Instrument Company, USA, may be used.

A suitable sample may be 1 inch (25.4) long (in direction of stretch, Y-direction) and having the width of the elastic material (15) plus along one longitudinal side of the sample some of the neighboring first sheet (13) and second sheet that is not part of the elasticized region (12), e.g. attached to said elastic material (15), e.g. 40 mm.

The sample is conditions for 16 hours at 50% relative humidity and 20° C.

Then the area formed by the first sheet and second sheet is carefully peeled open up to the elastic material; the peeled open area of the first sheet and second sheet are attached between the clamps of the test equipment, so that there is no slag in the sample. The test can then be run and the force to peel the elastic material and the first sheet and/or second sheet is recorded and reported as peel force value used herein. If the composite sheet allows more samples to be taken, then this test can be repeated for more samples, and the average peel force can be obtained, and reported herein as peel force values.

While particular embodiments of the present invention have been illustrated and described, it would be obvious to those skilled in the art that various other changes and modifications that are within the scope of this invention.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for making a composite sheet (10) useful for an absorbent article, said composite sheet (10) comprising one or more openings to receive fecal material, a wrinkled, patterned elasticized region (12) that comprises adhesive, a patterned first sheet (13) and an elastic material (15), said composite sheet (10) being obtained by:
   a. obtaining a first sheet (13);
   b. obtaining an elastic material (15) that is at least partially stretched;
   c. submitting said first sheet (13) or part thereof to a cooling, patterning, pressure-applying step to obtain a patterned first sheet (13) comprising troughs (16), and then positioning said at least partially stretched elastic material (15) adjacent said patterned first sheet (13) to obtain a combined material;
   d) simultaneously or subsequent to step c) attach at least a portion of the formed troughs (16) to said elastic material (15), to obtain a stretched composite sheet (10) comprising a patterned elasticized region;
   e) relaxing the composite sheet (10) of step d) to obtain a composite sheet (10) comprising a wrinkled, patterned elasticized region (12), said composite sheet (10) comprising one or more openings to receive fecal material.

2. The process of claim 1, wherein a first surface of said first sheet (13) or part thereof, that is not facing the elastic material (15), is pressurized by a first surface (31) of a first tool (30), the first surface of the first tool having a multitude of raised portions, whereby said raised portions form said troughs (16) in said first sheet (13) or part thereof; and wherein a second surface of said first sheet, facing the elastic material (15) is pressurized by a second, non-mating surface (35) of a second tool (34).

3. The process of claim 2, wherein said first tool (30) has a transverse axis (33) and said raised portions are in the form of: a) a multitude of ridges, each ridge being positioned under angle of between 0° to 45° with a line parallel to the transverse axis (33), and/or b) a multitude of teeth, positioned along the x and y direction of said tool's surface, in first rows positioned under angle of between 0° to 45° with a line parallel to the transverse axis (33) and second rows positioned perpendicular to said first rows.

4. The process of claim 3, wherein the distance between said raised portions and the second tool's surface (35) is 0.01 mm to 0.25 mm.

5. The process of claim 3, wherein said raised portions have a first dimension in a direction substantially perpendicular to the transverse axis (33) of the first tool (30) of from 0.1 to 1.0 mm, and said first sheet having a caliper of less than 40% of said first dimension.

6. The process of claim 2, wherein the pressure between the first and second surface or between the first surface and first sheet (13) is from 20,000 to 80,000 psi.

7. The process of claim 1, wherein the troughs (16) of the first sheet (13) have a higher density than the portions of the first sheet (13) not forming said troughs (16).

8. The process of claim 1, wherein said adhesive is in the form of filaments with an average diameter of less than 200 microns.

9. An absorbent article comprising a composite sheet (10) material obtained by the process of claim 1.

10. The absorbent article of claim 9, wherein the composite sheet (10) comprises one or more openings (11) to receive fecal material; a wrinkled, patterned elasticized region; a longitudinal direction Y and a transverse direction X; and a first sheet (13) and an elastic material (15), said elastic material (15) extending substantially in longitudinal direction and providing elasticity in substantially said longitudinal direction, at least a portion of said first sheet comprising a pattern of a multitude of troughs (16) and a multitude of crests (17) in at least the longitudinal direction, said troughs (16) of said first sheet (13) having a higher density than the crests (17) of said first sheet, wherein said elastic material (15) is attached to said troughs (16) of said first sheet.

11. The absorbent article of claim 10, wherein said first sheet (13) in said elasticized region (12) comprises, at an elongation of 66.67%, a uniform wrinkle pattern, having wrinkles of an average wrinkle height Hw of from 150 microns to 600 microns, or between at least 200 microns or at least 300 microns and/or up to 550 microns, or up to 500 microns, and having a wrinkle height standard deviation (STD) of less than 100 microns, and the RSD (being the STD/average Hw) is less than 20%.

12. The absorbent article of claim 9, wherein said first sheet (13) in said elasticized region (12) comprises, at an elongation of 66.67%, a uniform wrinkle pattern, having wrinkles with peaks and valleys, whereby the average distance between the highest points of neighboring peaks of the wrinkles is 800 to 1300 microns and whereby the standard deviation is less than 200 microns and whereby the RSD is less than 20%.

13. The absorbent article of claim 9, wherein said elasticized region (12) comprises adhesive filaments, having an average diameter of less than 200 microns, adhering the elastic material (15) and said troughs (16) of the first sheet.

14. The absorbent article of claim 9, wherein said composite sheet (10) is a composite barrier sheet, having a hydrostatic head of at least 15 mbar and/or said first sheet (13) is a barrier sheet having a hydrostatic head of at least 15 mbar.

15. The absorbent article of claim 9, wherein said first sheet (13) is a nonwoven sheet or nonwoven layer, having at least two spunbond webs and at least one meltblown web, said sheet or layer having a basis weight of at least 17 g/m2, and sheet or layer comprising at least 3 g/m2 meltblown fibers.

16. The absorbent article of claim 9, wherein said elastic material (15) is an elastic band with an average width of 3 mm to 25 mm and whereby the patterned first sheet (13) has a pattern with a width that is from 70% to 300% of the width of the elastic material (15).

17. The absorbent article of claim 9, wherein said composite sheet (10) has an elastic profile of: 1.5Lt by a first load force of less than 1.1N, 3.0Lt by a first load force of less than 2.1N and 4.5Lt by a first load force of less than 3.0N and a second unload force at 4.5Lt of more than 0.9N, a second unload force at 3.0Lt of more than 0.5N and a second unload force at 1.5Lt of more than 0.1N.

18. The absorbent article of claim 9, wherein whereby said elasticized region (12) has a residual strain of less than 20%.

19. The absorbent article of claim 9, wherein said composite sheet (10) comprises a slit opening (11) and at least two elasticized regions (12), each of said elasticized regions being positioned along one of the longitudinal sides of said slit opening (11).

20. An absorbent article comprising a composite sheet (10) that has one or more openings (11) and that comprises a patterned and wrinkled elasticized region (12), said elasticized region (12) containing adhesive, an elastic material (15) and a patterned and wrinkled first sheet (13), having troughs (16) that are attached or partially attached to said elastic material, and whereby said elasticized region (12) has a residual strain of less than 30%, and whereby said composite sheet (10) comprises a wrinkled second sheet (14), that may optionally be patterned, and whereby said elastic material (15) is positioned between said first sheet (13) and said second sheet (14), and whereby said elasticized region (12) has a peel force of at least 1.4 N.

* * * * *